(12) United States Patent
Bach et al.

(10) Patent No.: US 7,425,663 B2
(45) Date of Patent: Sep. 16, 2008

(54) METHOD FOR PRODUCTION PROPYLENE FROM A FLOW CONTAINING $C_4$ TO $C_8$ OLEFINS

(75) Inventors: Hermann Bach, Heiligenroth (DE); Harald Kömpel, Neu-Isenburg (DE); Bernd Ahlers, Frankfurt am Main (DE); Peter Trabold, Darmstadt (DE); Frank Höper, Karben (DE)

(73) Assignee: Lurgi AG, Frankfurt/Main (DE)

( * ) Notice: Subject to any disclaimer, the term of this patent is extended or adjusted under 35 U.S.C. 154(b) by 611 days.

(21) Appl. No.: 10/522,498

(22) PCT Filed: Jun. 5, 2003

(86) PCT No.: PCT/EP03/05903

§ 371 (c)(1),
(2), (4) Date: Jan. 13, 2005

(87) PCT Pub. No.: WO2004/009519

PCT Pub. Date: Jan. 29, 2004

(65) Prior Publication Data

US 2005/0234282 A1 Oct. 20, 2005

(30) Foreign Application Priority Data

Jul. 19, 2002 (DE) .................. 102 33 069

(51) Int. Cl.
*C07C 4/02* (2006.01)
*C10G 11/00* (2006.01)
*C10G 9/36* (2006.01)

(52) U.S. Cl. .......... 585/652; 585/653; 208/120.01; 208/130

(58) Field of Classification Search ............. 585/652, 585/653; 208/120.01, 130
See application file for complete search history.

(56) References Cited

U.S. PATENT DOCUMENTS 5,981,819 A * 11/1999 Moeller et al. ............. 585/653

* cited by examiner

*Primary Examiner*—Glenn Caldarola
*Assistant Examiner*—In Suk Bullock
(74) *Attorney, Agent, or Firm*—Jonathan Myers; Andrew Wilford

(57) ABSTRACT

In a method for the production of propylene, a charge stream containing $C_4$ to $C_6$ olefins is evaporated, superheated, mixed with hot water vapor, the olefins vapor mixture converted on a zeolite catalyst, the reaction mixture formed thereby cooled, and then partially condensed. In order to increase the yield of propylene, the gaseous phase containing ethylene, propylene, $C_4$ to $C_8$ olefins, and additional hydrocarbons that is accumulated during the partial condensation is compressed, the gaseous and liquid phase containing propylene, ethylene, and other light hydrocarbons that exit from the compression step is separated into a gaseous phase containing propylene, ethylene, and other light hydrocarbons and a liquid phase containing $C_4+$ olefins, and the liquid phase is separated into a fraction containing $C_4$ to $C_6$ olefins and a fraction containing $C_7+$ olefins.

5 Claims, 1 Drawing Sheet

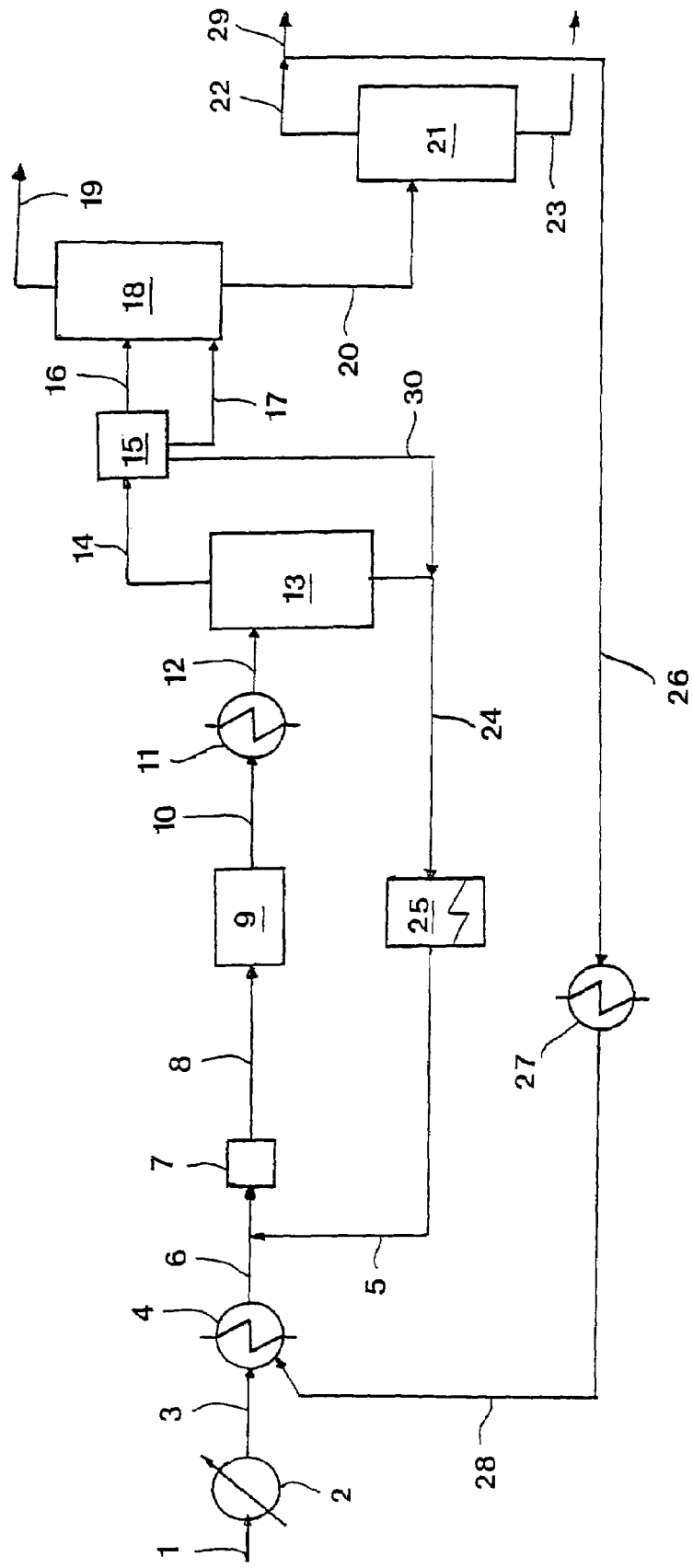

METHOD FOR PRODUCTION PROPYLENE FROM A FLOW CONTAINING $C_4$ TO $C_8$ OLEFINS

CROSS REFERENCE TO RELATED APPLICATIONS

This application is the U.S. national phase of PCT application PCT/EP2003/005903, filed 5 Jun. 2003, published 29 Jan. 2004 as WO 2004/009519, and claiming the priority of German patent application 10233069.7 itself filed 19 Jul. 2002.

The invention relates to a method for the production of propylene from a liquid charge stream containing $C_4$ to $C_8$ olefins that evaporates at 25 to 200° C. and is superheated to 350 to 400° C., wherein the formed vapor containing the olefins is mixed with hot water vapor, the olefins vapor mixture converted on a shape-selective, pentasil-type zeolite fixed-bed catalyst at inlet temperatures of 450 to 550° C. and pressures of 0.5 to 3.0 bar (abs), the reaction mixture formed thereby is cooled to 100 to 200° C., and through a subsequent further cooling to 40 to <100° C. a partial condensation is carried out with formation of a gaseous phase containing essentially ethylene, propylene, $C_4$ to $C_8$ olefins and additional hydrocarbons and a liquid phase that is essentially comprised of water and is returned into the charge stream.

In order to be able to satisfy the increasing demand worldwide for propylene that is accumulated to roughly 98% as a by-product during thermal cracking (Steamcracking) and during catalytic cracking in a fluid bed (Fluid Catalytic Cracking, FCC) of crude oil fractions, the experts aim to make propylenes in a secondary manner. For this purpose, according to Cit.:HYDROCARBON ENGINEERING May 1999, p. 66/67, $C_4+$ olefins, such as butylenes, pentenes, hexenes etc. are fragmented by means of a shape-selective, pentasil-type zeolite catalyst into "$CH_2$"-units that then recombine to propylene, ethylene, and butylene in a quasi-equilibrium distribution, whereby the conversion rate is approx. 83 percent by weight (42 percent by weight propylene, 31 percent by weight butylene, and 10 percent by weight ethylene) based on the olefins in the charge steam. In case of a return of butylene into the process cycle, even a yield of 60 percent by weight of propylene and 15 percent by weight of ethylene results. For the production of propylene, the charge stream containing $C_4+$ hydrocarbons that is mixed with returned butylene is evaporated after passing through a saturator, after addition of recycle water vapor, in a heat exchanger at temperatures of 20 to 100° C., subsequently superheated in a heat exchanger and in an oven to a temperature of 100 to 500° C., and then supplied to a reaction vessel filled with a ZSM-5-type shape-selective zeolite fixed-bed catalyst, preferably of the Claus-type. The gas stream exiting from the reaction vessel is cooled in a heat exchanger to a temperature of 100 to 200° C., compressed to a pressure of 2 to 6 bar (abs), afterwards charged to the condensation side of an evaporator/condenser and the hydrocarbons that remained in the gaseous phase directed to a gasoline/olefin-splitter, while the condensate that is primarily comprised of water is evaporated in the evaporator/condenser after a lowering of the pressure and supplied to the saturator as recycle water vapor. The gaseous phase is separated into a fraction containing $C_3$ hydrocarbons and gasoline in the splitter.

It is the object of the present invention to increase the yield of propylene by means of the method described in the beginning, without increasing the technical requirements.

The object is solved by compressing the gaseous phase that contains ethylene, propylene, $C_4$ to $C_8$ olefins and additional hydrocarbons formed in a partial condensation carried out by means of a quenching step to a pressure of 20 to 30 bar (abs), separating the gaseous and liquid phase exiting from the compression step into a gaseous phase containing essentially propylene, ethylene and other light hydrocarbons and a liquid phase containing $C_4+$ olefins, and separating the liquid phase into a fraction containing $C_4$ to $C_6$ olefins and a fraction containing $C_7+$ olefins.

A preferable embodiment of the method is to be seen therein, that the water stream accumulated as condensate in the quenching step is re-evaporated, then heated to a temperature of 600 to 800° C., and returned to the charge stream that contains vaporous hydrocarbons. By this measure, the charge stream is heated to the inlet temperature of 450 to 550° C. required for the reaction step, so that it can be done without the heating of the charge stream containing the hydrocarbons by means of a special oven.

According to another feature according to the invention, the majority of the produced $C_4$ to $C_6$ olefins is returned to the charge stream containing vaporous hydrocarbons, in order to further increase the yield of propylene.

It is further advantageous, to evaporate the water that accumulates in the compression step, to then heat the vapor to a temperature of 600 to 800° C. and re-add it to the charge stream containing vaporous hydrocarbons.

The invention is exemplary illustrated through a process diagram in the drawing and is further explained hereinafter.

The charge stream containing $C_4$ to $C_8$ olefins is charged via line (1) to an evaporator (2), in which it is heated to a temperature of 100° C. and evaporated at a pressure of 6.5 bar (abs). The charge stream flows via line (3) into a superheater (4), in which it is superheated to a temperature of 350° C. For further superheating of the charge stream to a temperature of 500° C., the charge stream is mixed with 700° C. hot water vapor that is supplied via line (5) and fed into line (6) by means of the mixing device (7). The gas stream that has a temperature of 500° C. is directed into the reactor (19) via line (8). In an endothermic adiabatic reaction on a zeolite fixed-bed catalyst, the majority of the $C_4$ to $C_8$ olefins is converted into $C_3$ to $C_6$ olefins with propylene as the main component. The reaction mixture that has a reaction temperature of 460° C. and is withdrawn via line (10) is cooled in the heat exchanger (11) to a temperature of 200° C. Subsequently, the reaction mixture is charged via line (12) to a quenching column (13), in which a cooling to 60° C. occurs at the head of the column. The gaseous phase accumulating in the quenching column (13) is supplied via line (14) to a compressor (15), compressed to a pressure of 27 bar (abs), and cooled to a temperature of 60° C. The gaseous and liquid phase containing hydrocarbons that are formed in the compressor (15) are fed via lines (16) and (17), respectively, into a distillation column (18), through the head of which via line (19) the gaseous phase that has a temperature of 20° C. and contains propylene, ethylene, and other light hydrocarbons, and from the bottom of which via line (20) a liquid phase that contains essentially $C_4+$ olefins are withdrawn. The head product has a propylene content of about 75 percent by weight. The bottom product is supplied to a distillation column (21), in which it is separated into a gaseous phase containing $C_4$ to $C_6$ olefins with a temperature of 50° C. and a liquid phase containing $C_7+$ olefins. The gaseous phase that exits from the distillation column (21) via line (22) is charged to about 65% via line (26) to a superheater (27) and afterwards is returned via line (28) to the heat exchanger (4) for the superheating of the vaporous charge stream, while the remainder of the gaseous phase is discharged via line (29). The liquid phase that is leaving the distillation column (21) is recovered from the process via line (23). The water stream exiting from the quenching column (13) is directed via line (24) into the evaporator (25), and the water vapor formed therein that after superheating has a temperature of 700° C. is added via line (5) to the charge stream containing vaporous hydrocarbons and having a temperature of 350° C., before the charge stream flows into the mixing device (7). The water that is formed in the compressor (15) is fed via line (30) into the water stream that is withdrawn from the quenching column (13) through line (24).

The invention claimed is:

1. A method for producing a hydrocarbon mixture rich in propylene, consisting essentially of propylene, ethylene and other light hydrocarbons from a liquid charge stream containing $C_4$ to $C_8$ olefins, which comprises the steps of:
   (a) charging the liquid charge stream containing $C_4$ to $C_8$ hydrocarbons into an evaporator at a temperature of 25 to 200° C. to evaporate the liquid stream;
   (b) superheating the evaporated liquid stream at a temperature of 350 to 400° C. followed by an additional superheating of the evaporated liquid stream to 450 to 550° C. using hot water vapor; to form an olefin—water vapor mixture;
   (c) adiabatically reacting the olefin—water vapor mixture, superheated according to step (b), over a shape-selective, pentasil zeolite fixed-bed catalyst to convert a majority of the $C_4$ to $C_8$ olefins in the olefin—water vapor mixture to a mixture of $C_3$ to $C_6$ olefins rich in propylene;
   (d) following step (c), cooling the olefin—water vapor mixture to a temperature of 100 to 200° C.;
   (e) quenching the olefin—water vapor mixture cooled according to step (d), to a temperature of 40 to <100° C., to partially condense the olefin—water vapor mixture; thereby obtaining a gaseous hydrocarbon phase consisting essentially of ethylene, propylene, $C_4$ to $C_8$ olefins and additional hydrocarbons and, a liquid phase consisting essentially of water that is returned to the evaporated liquid stream during step (b);
   (f) compressing the gaseous hydrocarbon phase obtained according to step (e) at a pressure of 20 to 30 bar absolute to remove accumulated water from the gaseous hydrocarbon phase to obtain a mixture of gaseous and liquid hydrocarbon phases;
   (g) separating the mixture of gaseous and liquid hydrocarbon phases into a gaseous hydrocarbon phase, rich in propylene, consisting essentially of propylene, ethylene, and other light hydrocarbons, and recovering said gaseous hydrocarbon phase and a liquid hydrocarbon phase containing $C_4+$ olefins; and
   (h) separating the liquid hydrocarbon phase into a fraction containing $C_4$ to $C_6$ olefins and a fraction containing $C_7+$ olefins.

2. The method defined in claim 1, wherein according to step (e) the liquid phase consisting essentially of water accumulated as a condensate during the quenching is reevaporated, then heated to a temperature of 600 to 800° C., and then returned to the liquid evaporated stream during step (b).

3. The method defined in claim 1, wherein following step (h) the majority of the generated $C_4$ to $C_6$ olefins is returned to the liquid charge stream according to step (a).

4. The method defined in claim 1, wherein according to step (f) the accumulated water, separated from the gaseous and liquid hydrocarbon phases is evaporated, then heated to a temperature of 600 to 800° C., and returned to the liquid evaporated stream during step (b).

5. The method defined in claim 1 wherein according to step (g) the gaseous hydrocarbon phase, rich in propylene consists essentially of 75% propylene.

* * * * *